US011782108B2

(12) United States Patent
Lau et al.

(10) Patent No.: US 11,782,108 B2
(45) Date of Patent: *Oct. 10, 2023

(54) HEAD COIL SYSTEM AND METHODS FOR ENHANCING AND/OR OPTIMIZING MRI

(71) Applicant: SYNAPTIVE MEDICAL INC., Toronto (CA)

(72) Inventors: William Wai-Leung Lau, Toronto (CA); Alexander Gyles Panther, Toronto (CA); Gilbert Thevathasan, Toronto (CA); Mark Tullio Morreale, Toronto (CA)

(73) Assignee: Synaptive Medical Inc.

( * ) Notice: Subject to any disclaimer, the term of this patent is extended or adjusted under 35 U.S.C. 154(b) by 0 days.

This patent is subject to a terminal disclaimer.

(21) Appl. No.: 17/818,380

(22) Filed: Aug. 9, 2022

(65) Prior Publication Data
US 2022/0381858 A1    Dec. 1, 2022

Related U.S. Application Data

(63) Continuation of application No. 15/781,405, filed as application No. PCT/IB2016/050407 on Jan. 27, 2016, now Pat. No. 11,435,418.

(51) Int. Cl.
*A61B 5/055* (2006.01)
*G01R 33/34* (2006.01)
(Continued)

(52) U.S. Cl.
CPC ........ *G01R 33/34084* (2013.01); *A61B 5/055* (2013.01); *G01R 33/34007* (2013.01);
(Continued)

(58) Field of Classification Search
CPC ........ G01R 33/34084; G01R 33/34046; G01R 33/3642; A61B 5/055; A61B 90/14; A61B 90/16; A61B 2090/374
See application file for complete search history.

(56) References Cited

U.S. PATENT DOCUMENTS 6,975,115 B1 * 12/2005 Fujita ................. G01R 33/3415
                                                          324/309
7,450,985 B2 * 11/2008 Meloy .................... A61G 7/072
                                                          128/870

(Continued)

OTHER PUBLICATIONS

Meloy, "Nomoco Pillow Demonstration Video" YouTube Aug. 9, 2013 https://youtu.be/MrOV75J3KvQ (Year: 2013).*

(Continued)

*Primary Examiner* — Colin T. Sakamoto

(57) ABSTRACT

An adjustable head coil system and methods for enhancing and/or optimizing magnetic resonance imaging, involving a housing, the housing having at least one portion, the at least one portion having a lower portion, an upper portion, and opposing side portions, each at least one portion optionally in movable relation to any other portion for facilitating adjustability, each at least one portion configured to accommodate at least one radio-frequency coil, and the upper and lower portions each optionally configured to overlap and engage the opposing side portions for facilitating decoupling the at least one radio-frequency coil, and a tongue portion optionally in movable relation to any other portion for facilitating adjustability, engageable with the lower portion, and fixably couple-able with a transporter.

20 Claims, 13 Drawing Sheets

(51) Int. Cl.
*G01R 33/36* (2006.01)
*A61B 90/16* (2016.01)
*A61B 90/00* (2016.01)
*A61B 90/14* (2016.01)

(52) U.S. Cl.
CPC ... *G01R 33/34046* (2013.01); *G01R 33/3642* (2013.01); *A61B 90/14* (2016.02); *A61B 90/16* (2016.02); *A61B 2090/374* (2016.02)

(56) References Cited

U.S. PATENT DOCUMENTS

| | | | | |
|---|---|---|---|---|
| 2005/0107686 | A1* | 5/2005 | Chan | G01R 33/3415 600/422 |
| 2007/0270683 | A1* | 11/2007 | Meloy | A61G 13/121 5/601 |
| 2009/0216110 | A1* | 8/2009 | Piron | A61B 5/055 600/422 |
| 2012/0293176 | A1* | 11/2012 | Zink | G01R 33/34007 324/322 |
| 2013/0076358 | A1* | 3/2013 | Taracila | G01R 33/34084 324/322 |

OTHER PUBLICATIONS

Philips, dStream T/R Head coil product brochure. Sep. 2015 (Year: 2015).*

William Wai-Leung Lau et al, "Head Coil System and Methods for Enhancing and/or Optimizing MRI", U.S. Appl. No. 15/781,405, filed Jun. 4, 2018, Notice of Allowance issued.

* cited by examiner

HEAD COIL SYSTEM AND METHODS FOR ENHANCING AND/OR OPTIMIZING MRI

CROSS-REFERENCE TO RELATED APPLICATION(S)

This document is a continuation application, claiming the benefit of, and priority to U.S. patent application Ser. No. 15/781,405, titled "HEAD COIL SYSTEM AND METHODS FOR ENHANCING AND/OR OPTIMIZING MRI," filed on Jun. 4, 2018, and International Application No. PCT/IB2016/050407, titled "HEAD COIL SYSTEM AND METHODS FOR ENHANCING AND/OR OPTIMIZING MRI," filed on Jan. 27, 2016, both of which are hereby incorporated by reference herein in their entirety.

FIELD

The present disclosure technically relates to the field of magnetic resonance imaging (MRI) systems and methods. More particularly, the present disclosure technically relates to the field of radiofrequency (RF) coil systems and methods for MRI. Even more particularly, the present disclosure technically relates to the field of radio-frequency head coil systems and methods for MRI.

BACKGROUND

In the related art, RF coils are the receivers, and sometimes also the transmitters, RF signals in the field of MRI. The magnetic resonance (MR) signal in MRI is generated by way of resonance emitted by radio frequency coils which typically involve two types of electromagnetic coils, transmitter coils and receiver coils, respectively generating and receiving signals corresponding to electromagnetic fields. Atomic nuclei have distinctive resonant frequencies in the RF portion of the electromagnetic spectrum for use in MRI.

Referring to FIG. 1, this diagram illustrates an MRI "head coil" or an MRI "brain coil" 5 that typically has a birdcage configuration, in accordance with the related art. These related art head coils are cumbersome and also cause various types of physical and emotional distress in a subject, such as a patient, including claustrophobia. Referring physicians, radiologists, and MRI technologists currently attempt to manage affected patients by understanding the etiology of the problem and attempting an appropriate maneuver or an appropriate intervention to counteract the condition. However, any such efforts are limited by the physical constraints of related art MRI equipment. Since many of the birdcage-style head coils are rigid and fabricated to fit a regularly shaped median-size head, subjects whose head is either larger or irregularly shaped may suffer physical distress from the ill-fitting related art head coil.

In related art MRI equipment, "psychological distress" experienced by a subject in the MR environment includes all subjectively unpleasant experiences attributable to a procedure. For instance, a patient may experience distress ranging from mild anxiety to a serious panic attack, whereby psychiatric intervention or medication is necessitated. Severe psychological reactions to MR examinations are characterized by the rapid onset of at least four of the following symptoms: nausea, paresthesia, palpitations, chest pain, faintness, dyspnea, choking sensation, sweating, trembling, vertigo, depersonalization, fear of losing control, or fear of dying.

Specifically, an ill-fitting related art head coil is likely to cause claustrophobia in many patients who are predisposed to anxiety disorders, wherein claustrophobia may be characterized by the marked, persistent, and excessive fear of enclosed spaces. In such affected individuals, exposure to an enclosed space, such as within MRI machines, especially within related art MRI head coils, tends to provoke an immediate anxiety response that may rise to the level of a panic attack. Considerable time is expended be medical personnel in attempting to ameliorate such distress, usually resulting in compromising the imaging.

Accordingly, MRI head coils have experienced many challenges in the related art, such as adequate accommodation of a patient's head in terms of both volume and shape, limited maneuverability, limited to non-existent adjustability, and a requirement that a patient's head is disposed into related art coils, and the requirement that, if a patient is already lying down, the patient must rise to place the related art underneath the patient's head in order to dispose the patient's head into the related art coils, thereby adversely affecting patient comfort as well as image quality.

SUMMARY

The present disclosure addresses at least many of the foregoing challenges experienced by related art MRI head coils, by way of a head coil system and methods for enhancing and optimizing MRI that are readily implementable in relation to newly manufactured MRI machines or readily retrofittable in relation to existing MRI machines. The presently disclosed adjustable head coil system and methods for enhancing and optimizing MRI adapt an MRI machine to perform with increased efficiency and accuracy by way of better accommodating a patient head and by better disposing RF coils in relation to the patient head. To date, these capabilities have been hitherto unavailable in the related art.

In accordance with an embodiment of the present disclosure, a coil system for enhancing and/or optimizing magnetic resonance imaging comprises: a housing comprising a plurality of housing portions, the plurality of housing portions comprising a lower housing portion, an upper housing portion, and opposing side housing portions, each housing portion configured to accommodate at least one RF coil, the upper and lower housing portions each configured to overlap and engage the opposing side housing portions for facilitating decoupling the at least one RF coil, and the lower housing portion configured to engage with the opposing side housing portions; and a tongue portion in movable relation to each housing portion for facilitating adjustability, the tongue portion configured to: slidably engage with the lower housing portion, fixably couple with a transporter, and overlap each opposing side housing portion in a closed position, each housing portion further configured to independently move in relation to any other housing portion and in relation to the tongue portion for facilitating adjustability, each housing portion configured to overlap another housing portion in a closed position, the tongue portion comprising an overlapping lip structure and configured to overlap and engage the opposing side housing portions by way of the overlapping lip structure for eliminating any gaps between each at least one RF coil and ensuring decoupling of each at least one RF coil in the closed position, and the tongue portion configured to facilitate adjustability by way of at least one fine adjustment feature comprising at least one of an elastic material and a polymeric material having a memory property.

In accordance with an embodiment of the present disclosure, a method of fabricating a coil system for enhancing and/or optimizing magnetic resonance imaging comprises: providing a housing, providing the housing comprising providing a plurality of housing portions, providing the plurality of housing portions comprising providing a lower housing portion, an upper housing portion, and opposing side housing portions, providing the plurality of housing portions comprising: configuring each housing portion to accommodate at least one RF coil, configuring each of the upper and lower housing portions to overlap and engage the opposing side housing portions for facilitating decoupling the at least one RF coil, and configuring the lower housing portion to engage with the opposing side housing portions; and providing a tongue portion in movable relation to each housing portion for facilitating adjustability, providing the tongue portion comprising configuring the tongue portion to: slidably engage with the lower housing portion, fixably couple with a transporter, and overlap each opposing side housing portion in a closed position, providing the plurality of housing portions further comprising configuring each housing portion to independently move in relation to any other housing portion and in relation to the tongue portion for facilitating adjustability, providing the plurality of housing portions further comprising configuring each housing portion to overlap another housing portion in a closed position, providing the tongue portion comprising providing an overlapping lip structure and configuring the tongue portion to overlap and engage the opposing side housing portions by way of the overlapping lip structure for eliminating any gaps between each at least one RF coil and ensuring decoupling of each at least one RF coil in the closed position, and providing the tongue portion comprising configuring the tongue portion to facilitate adjustability by way of at least one fine adjustment feature comprising at least one of an elastic material and a polymeric material having a memory property.

In accordance with an embodiment of the present disclosure, a method of enhancing and/or optimizing magnetic resonance imaging by way of a coil system, comprises: providing the coil system, providing the coil system comprising: providing a housing, providing the housing comprising providing a plurality of housing portions, providing the plurality of housing portions comprising providing a lower housing portion, an upper housing portion, and opposing side housing portions, providing the plurality of housing portions comprising: configuring each housing portion to accommodate at least one RF coil, configuring each of the upper and lower housing portions to overlap and engage the opposing side housing portions for facilitating decoupling the at least one RF coil, and configuring the lower housing portion to engage with the opposing side housing portions; and providing a tongue portion in movable relation to each housing portion for facilitating adjustability, providing the tongue portion comprising configuring the tongue portion to: slidably engage with the lower housing portion, fixably couple with a transporter, and overlap each opposing side housing portion in a closed position, providing the plurality of housing portions further comprising configuring each housing portion to independently move in relation to any other housing portion and in relation to the tongue portion for facilitating adjustability, providing the plurality of housing portions further comprising configuring each housing portion to overlap another housing portion in a closed position, providing the tongue portion comprising providing an overlapping lip structure and configuring the tongue portion to overlap and engage the opposing side housing portions by way of the overlapping lip structure for eliminating any gaps between each at least one RF coil and ensuring decoupling of each at least one RF coil in the closed position, and providing the tongue portion comprising configuring the tongue portion to facilitate adjustability by way of at least one fine adjustment feature comprising at least one of an elastic material and a polymeric material having a memory property; and operating the coil system.

Some of the features in the present disclosure are broadly described in order that the section entitled Detailed Description is better understood and that the present contribution to the art is better appreciated. Additional features of the present disclosure are hereinafter described. In this respect, the present disclosure is not limited in its implementation to the details of the components or steps set forth herein or as illustrated in the several figures of the Drawing(s) and that the components or steps may be carried out in various ways. Also, the phraseology and terminology employed herein are for the purpose of the description and should not be regarded as limiting.

BRIEF DESCRIPTION OF THE DRAWING(S)

The above, and other, aspects, features, and advantages of the several embodiments in the present disclosure will be more apparent from the below Detailed Description as presented in conjunction with the following brief description of the several figures of the Drawing(s).

Figure 1:
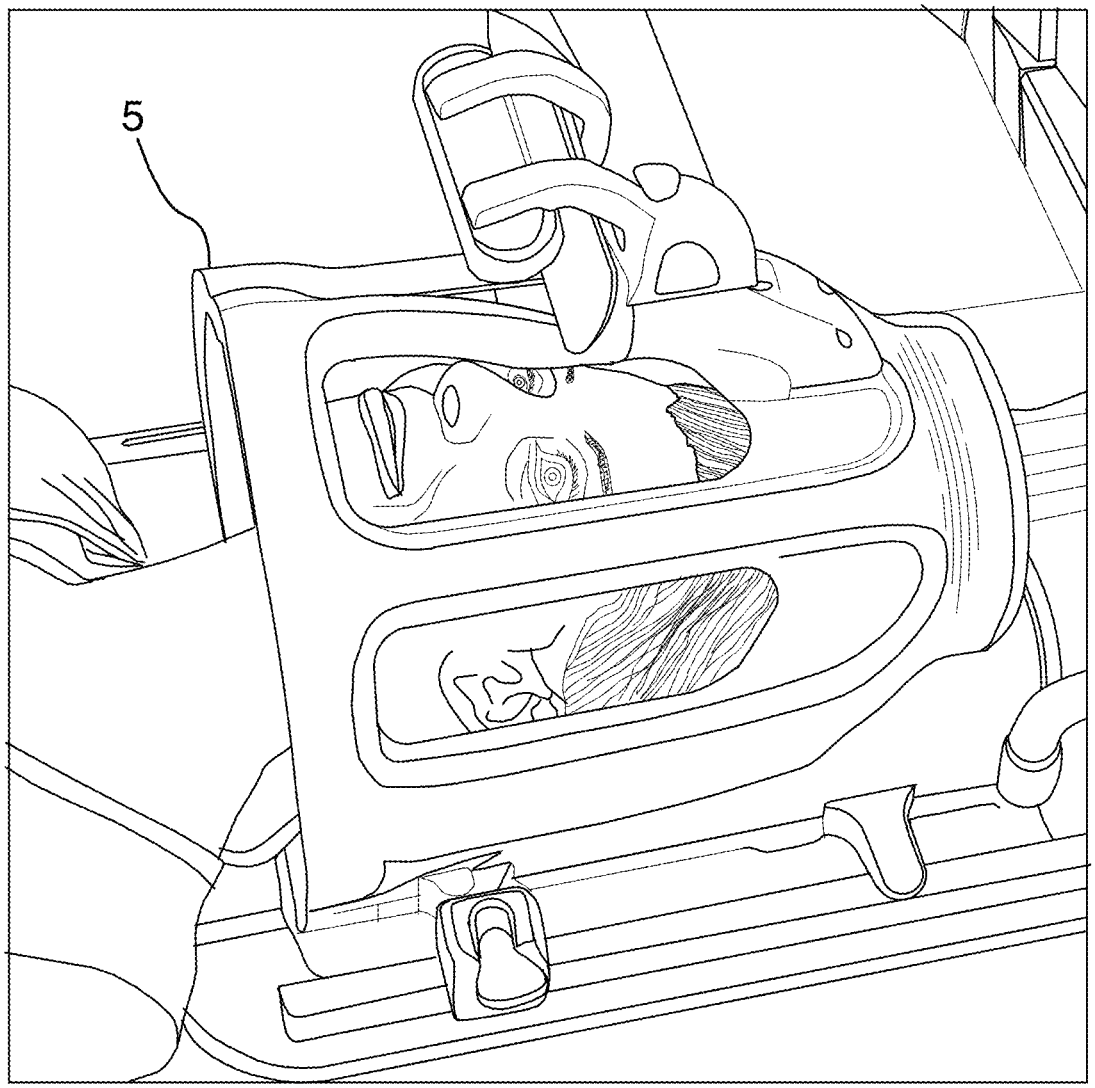
FIG. 1 is a diagram illustrating, in a perspective view, an MRI "head coil" or an MRI "brain coil" having a birdcage configuration, typically stored in a separate cabinet until ready for use, in accordance with the related art.

Corresponding reference numerals or characters indicate corresponding components throughout the several figures of the Drawing(s). Elements in the several figures are illustrated for simplicity and clarity and are not necessarily drawn to scale. For example, the dimensions of some elements in the figures may be emphasized relative to other elements for facilitating understanding of the various presently disclosed embodiments. Also, common, but well-understood, elements that are useful or necessary in commercially feasible embodiments are often not depicted in order to facilitate a less obstructed view of these various embodiments of the present disclosure.

DETAILED DESCRIPTION

The present disclosure generally involves a head coil system and methods for enhancing and/or optimizing MRI that is readily implementable in relation to newly manufactured MRI machines or readily retrofittable in relation to existing MRI machines. The presently disclosed head coil system and methods for enhancing and/or optimizing MRI may adapt an MRI machine to perform with an increased efficiency and an increased accuracy by at least better accommodating a patient head and by better disposing RF coils in relation to the patient head.

Figure 2:
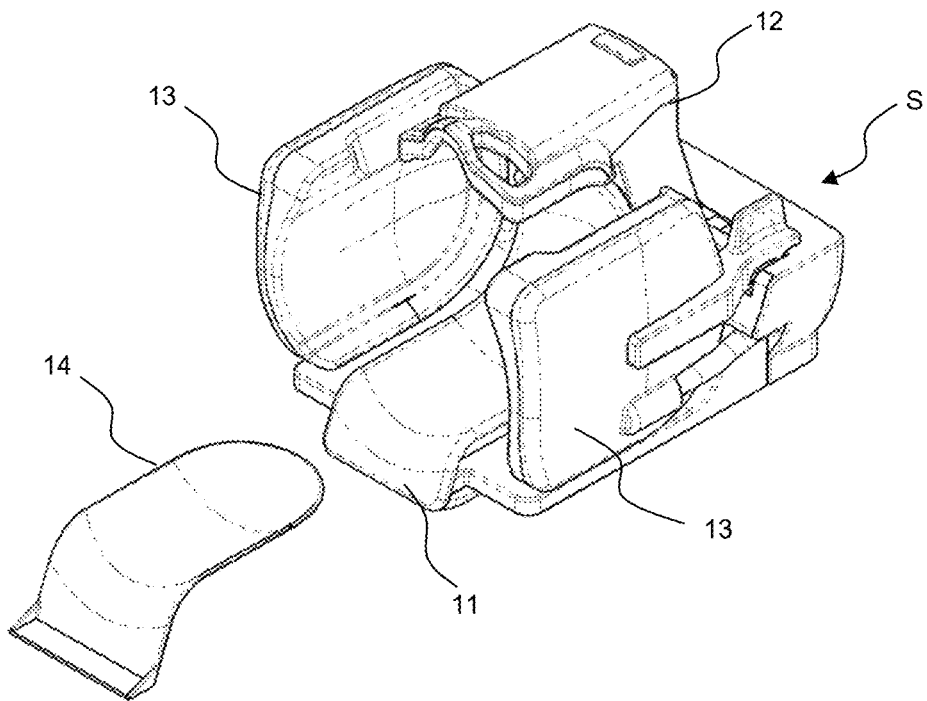
FIG. 2 is a diagram illustrating a perspective view of a head coil system for enhancing and/or optimizing MRI in an open position, in accordance with an embodiment of the present disclosure.

Referring to FIG. 2, this diagram illustrates, in a perspective view, a head coil system S for enhancing and/or optimizing MRI in an open position, in accordance with an embodiment of the present disclosure. The optionally adjustable head coil system S for enhancing and/or optimizing magnetic resonance imaging, comprises: a housing 10, the housing 10 comprising at least one portion, the at least one portion comprising portions, such as a lower portion 11, an upper portion 12, and opposing side portions 13, each at least one portion optionally in movable relation to any other portion for facilitating adjustability, each at least one portion configured to accommodate at least one RF coil 20, and the upper portion 12 and the lower portion 11 each optionally configured to overlap and engage the opposing side portions 13 for facilitating decoupling the at least one RF coil 20; and a tongue portion 14 optionally in movable relation to any other at least one portion for facilitating at least one of adjustability and dockability, engageable with the lower portion 11, and fixably couple-able with a transporter T. At least one of each at least one portion, such as a lower portion 11, an upper portion 12, and opposing side portions 13, and the tongue portion 14 is configured to be spaced apart in relation to another at least one portion, such as a lower portion 11, an upper portion 12, and opposing side portions 13, in an open position.

Still referring to FIG. 2, in accordance with an embodiment of the present disclosure, a coil system S for enhancing and/or optimizing magnetic resonance imaging comprises: a housing 10 comprising a plurality of housing portions, the plurality of housing portions comprising a lower housing portion 11, an upper housing portion 12, and opposing side housing portions 13, each housing portion configured to accommodate at least one RF coil 20, the upper and lower housing portions 12, 11 each configured to overlap and engage the opposing side housing portions 13 for facilitating decoupling the at least one RF coil 20, and the lower housing portion 11 configured to engage with the opposing side housing portions 13; and a tongue portion 14 in movable relation to each housing portion for facilitating adjustability, the tongue portion 14 configured to: slidably engage with the lower housing portion 11, fixably couple with a transporter T, and overlap each opposing side housing portion 13 in a closed position, each housing portion further configured to independently move in relation to any other housing portion and in relation to the tongue portion 14 for facilitating adjustability, each housing portion configured to overlap another housing portion in a closed position, the tongue portion 14 comprising an overlapping lip structure and configured to overlap and engage the opposing side housing portions 13 by way of the overlapping lip structure for eliminating any gaps between each at least one RF coil 20 and ensuring decoupling of each at least one RF coil 20 in the closed position, and the tongue portion 14 configured to facilitate adjustability by way of at least one fine adjustment feature comprising at least one of an elastic material and a polymeric material having a memory property.

Figure 3:
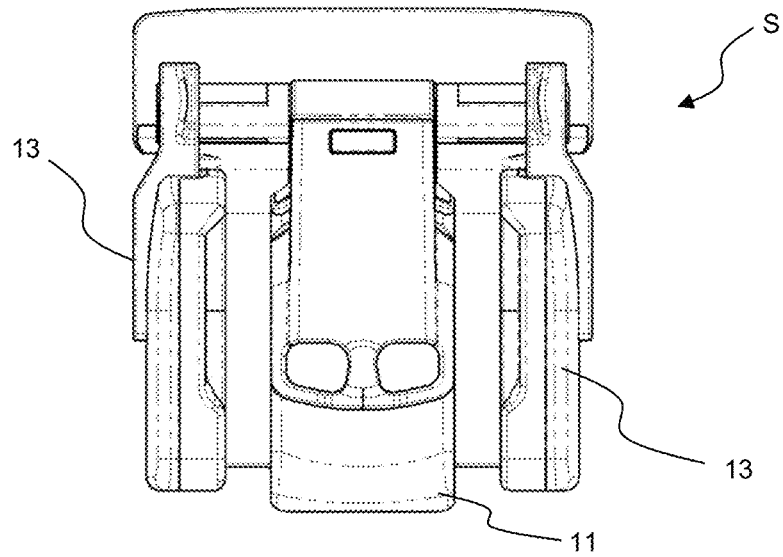
FIG. 3 is a diagram illustrating a top view of a head coil system for enhancing and/or optimizing MRI in an open position, as shown in FIG. 2, in accordance with an embodiment of the present disclosure.

Referring to FIG. 3, this diagram illustrates, in a bottom view, a head coil system S for enhancing and/or optimizing MRI in an open position, as shown in FIG. 2, in accordance with an embodiment of the present disclosure. The optionally adjustable head coil system S further comprises at least one of: at least one guide (not shown) configured to engage at least one corresponding rail 30 of the transporter T and to align the tongue portion 14 with the lower portion 11 and the opposing side portions 13; and at least one rail (not shown) configured to engage at least one corresponding guide (not shown) of the transporter T and to align the tongue portion 14 with the lower portion 11 and the opposing side portions 13 (See also FIGS. 10, 11, and 14).

Figure 4:
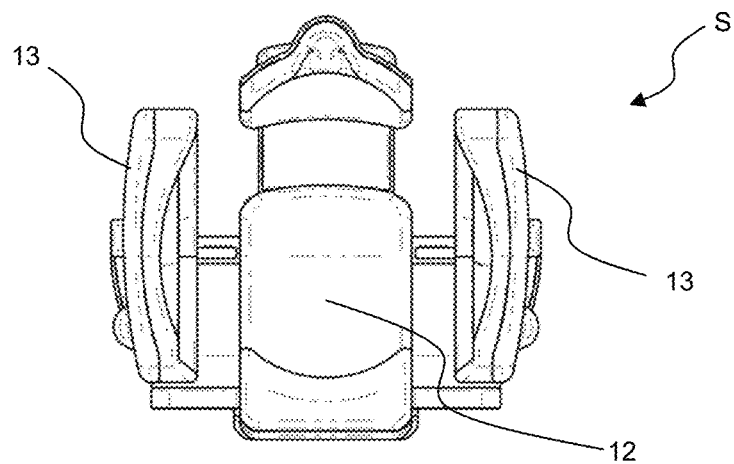
FIG. 4 is a diagram illustrating a front view of a head coil system for enhancing and/or optimizing MRI in an open position, as shown in FIG. 2, in accordance with an embodiment of the present disclosure.

Referring to FIG. 4, this diagram illustrates, in a top view, a head coil system S for enhancing and/or optimizing MRI in an open position, as shown in FIG. 2, in accordance with an embodiment of the present disclosure. The head coil system S is optionally adjustable. The housing 10 is configured to accommodate a head of any given subject by way of adjustability of each at least one portion in relation to another at least one portion, such as a lower portion 11, an upper portion 12, and opposing side portions 13. Further, at least one of each at least one portion, such as a lower portion 11, an upper portion 12, and opposing side portions 13, and the tongue portion 14 is configured to further facilitate adjustability by way of at least one fine adjustment feature (not shown) comprising at least of an elastic material, a polymeric material having a memory property, and at least one sub-portion (not shown) configured to articulate in relation to another sub-portion, whereby further adjustment is eliminable, and whereby scanning time is minimizable.

Figure 5:
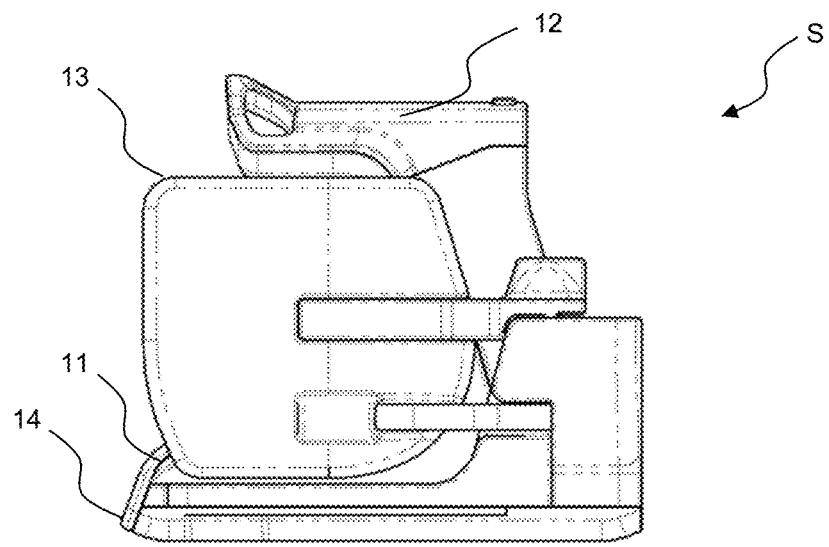
FIG. 5 is a diagram illustrating a side view of a head coil system for enhancing and/or optimizing MRI in an open position, an opposing side view being substantially symmetric, as shown in FIG. 2, in accordance with an embodiment of the present disclosure.

Referring to FIG. 5, this diagram illustrates, in a side view, a head coil system S or enhancing and/or optimizing MRI in an open position, an opposing side view being substantially symmetric, as shown in FIG. 2, in accordance with an embodiment of the present disclosure. The head coil system S is optionally adjustable. Each at least one portion, such as a lower portion 11, an upper portion 12, and opposing side portions 13, is configured to articulate in relation to another at least one portion by way of at least one of a hinge, a pin, a ball joint, and a slider. Further, each at least one sub-portion, e.g., of the lower portion 11, the upper portion 12, the opposing side portions 13, and even the tongue portion 14, is configured to articulate in relation to another at least one sub-portion (not shown) by way of at least one of a hinge, a pin, a ball joint, and a slider.

Figure 6:
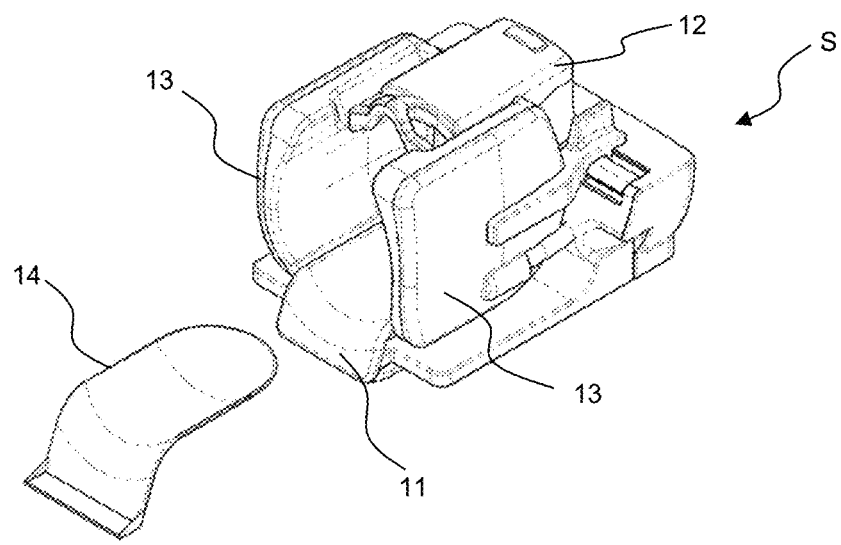
FIG. 6 is a diagram illustrating a perspective view of a head coil system for enhancing and/or optimizing MRI in a closed position, in accordance with an embodiment of the present disclosure.

Referring to FIG. 6, this diagram illustrates, in a perspective view, a head coil system S for enhancing and/or optimizing MRI in a closed position, in accordance with an embodiment of the present disclosure. The head coil system S is optionally adjustable. The optionally adjustable head coil system S for enhancing and/or optimizing magnetic resonance imaging, comprises: a housing 10, the housing 10 comprising at least one portion, the at least one portion comprising portions, such as a lower portion 11, an upper portion 12, and opposing side portions 13, each at least one portion optionally in movable relation to any other at least one portion for facilitating adjustability, each at least one portion configured to accommodate at least one RF coil 20, the upper portion 12 and the lower portion 11 each optionally configured to overlap and engage the opposing side portions 13 for facilitating decoupling the at least one RF coil 20, the lower portion 11 optionally engageable with the opposing side portions 13; and a tongue portion 14 optionally in movable relation to any other portion for facilitating at least one of adjustability and dockability, engageable with the lower portion 11, and fixably couple-able with a transporter T.

Figure 15:
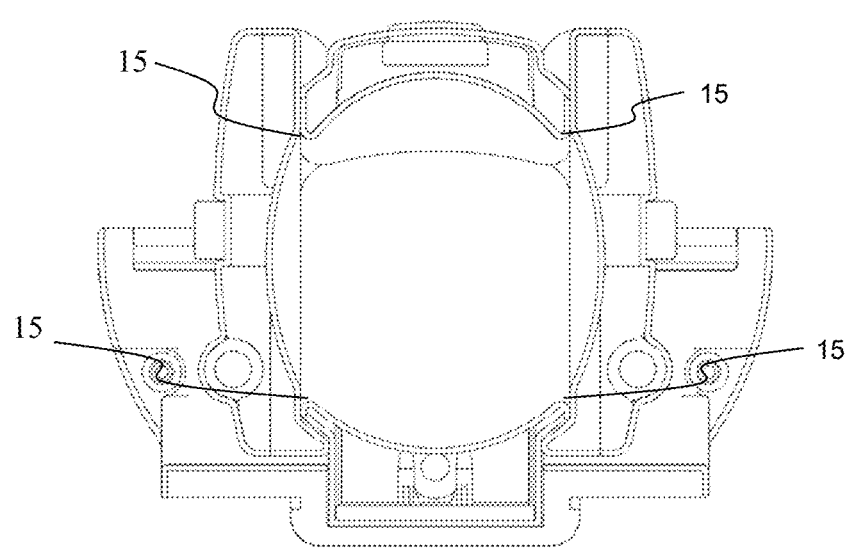
FIG. 15 is a diagram illustrating a section view of a head coil system for enhancing and/or optimizing MRI in a closed position, wherein at least one overlapping portion, such as at least one overlapping lip, forms a cavity, such as a substantially circular scanning surface or scanning bore, in accordance with an embodiment of the present disclosure.

Still referring to FIG. 6, at least one of each at least one portion, such as a lower portion 11, an upper portion 12, and opposing side portions 13, and the tongue portion 14 is optionally configured to be closed together in relation to another at least one portion, such as a lower portion 11, an upper portion 12, and opposing side portions 13, in an open position, and the tongue portion 14 is optionally configured to overlap and engage the opposing side portions 13 by way of an overlapping lip structure 15 for eliminating any gaps between each at least one RF coil 20 and ensuring decoupling of each at least one RF coil 20 in the closed position, whereby a scanning volume V, such as a substantially circular scanning, is provided (See also FIG. 15).

Figure 7:
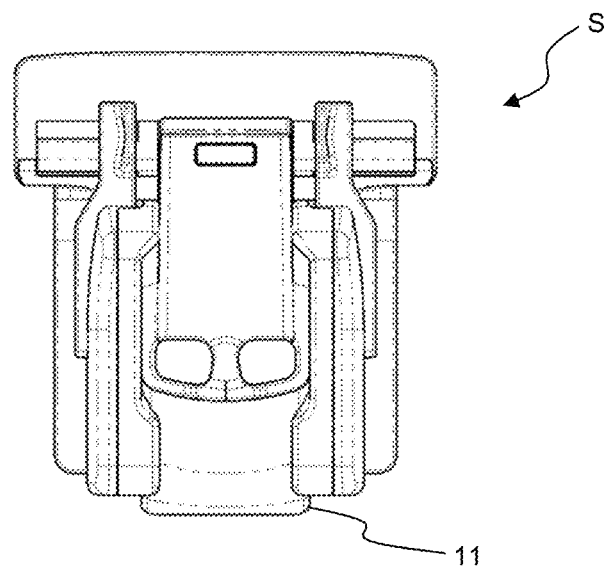
FIG. 7 is a diagram illustrating a top view of a head coil system for enhancing and/or optimizing MRI in a closed position, as shown in FIG. 6, in accordance with an embodiment of the present disclosure.

Referring to FIG. 7, this diagram illustrates, in a bottom view, a head coil system S for enhancing and/or optimizing MRI in a closed position, as shown in FIG. 6, in accordance with an embodiment of the present disclosure. The head coil system S is optionally adjustable. At least one of each at least one portion, such as the lower portion 11, the upper portion 12, and the opposing side portions 13, and the tongue portion 14 is optionally configured to overlap in relation to another at least one portion, such as the lower portion 11, the upper portion 12, and the opposing side portions 13, in a closed position.

Figure 8:
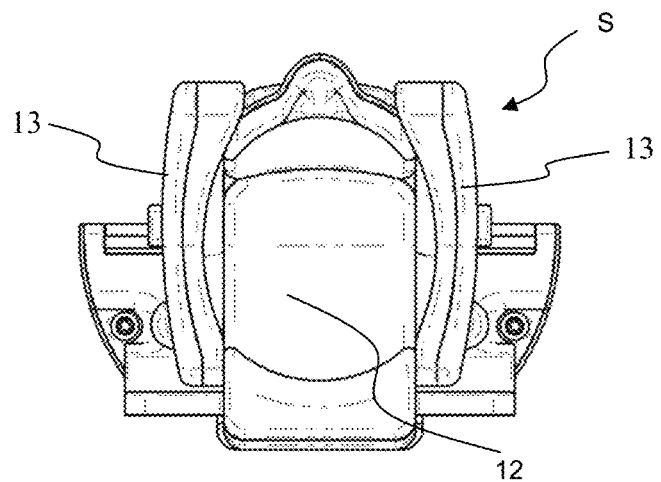
FIG. 8 is a diagram illustrating a front view of a head coil system for enhancing and/or optimizing MRI in a closed position, as shown in FIG. 6, in accordance with an embodiment of the present disclosure.

Referring to FIG. 8, this diagram illustrates, in a top view, a head coil system S for enhancing and/or optimizing MRI in a closed position, as shown in FIG. 6, in accordance with an embodiment of the present disclosure. The head coil system S is optionally adjustable. At least one of the upper portion 12, the lower portion 11, and the tongue portion 14 is optionally configured to overlap and engage the opposing side portions 13 by way of an overlapping lip structure 15 for eliminating any gaps between each at least one RF coil 20 and ensuring decoupling of each at least one RF coil 20 in the closed position.

Figure 9:
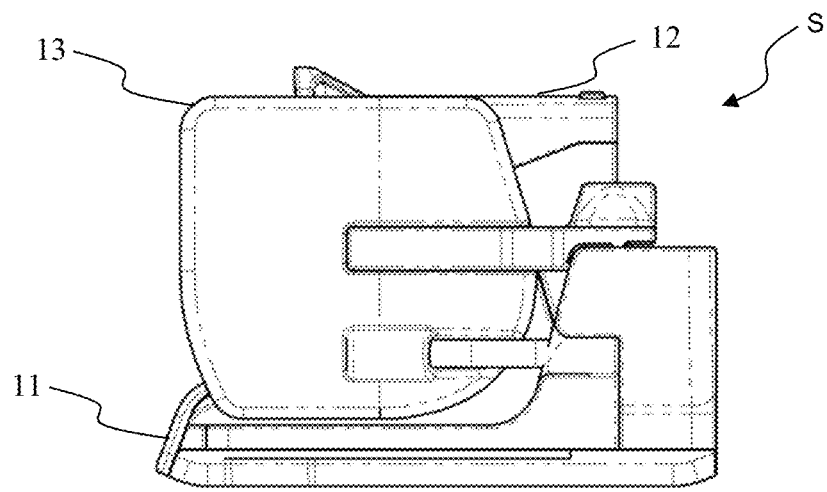
FIG. 9 is a diagram illustrating a side view of a head coil system for enhancing and/or optimizing MRI in a closed position, as shown in FIG. 6, an opposing side view being substantially symmetric, in accordance with an embodiment of the present disclosure.

Referring to FIG. 9, this diagram illustrates, in a side view, a head coil system S for enhancing and/or optimizing MRI in a closed position, as shown in FIG. 6, an opposing side view being substantially symmetric, in accordance with an embodiment of the present disclosure. The head coil system S is optionally adjustable. Each at least one portion, such as a lower portion 11, an upper portion 12, and opposing side portions 13, is optionally configured to articulate in relation to another portion (such as for adjusting size and shape to provide a best fit for a given head, and for facilitating closing of the housing 10) by way of at least one of a hinge, a pin, a ball joint, and a slider. Further, each at least one sub-portion, e.g., of the lower portion 11, the upper portion 12, the opposing side portions 13, and even the tongue portion 14, is optionally configured to articulate in relation to another sub-portion (not shown) by way of at least one of a hinge, a pin, a ball joint, and a slider.

Figure 10:
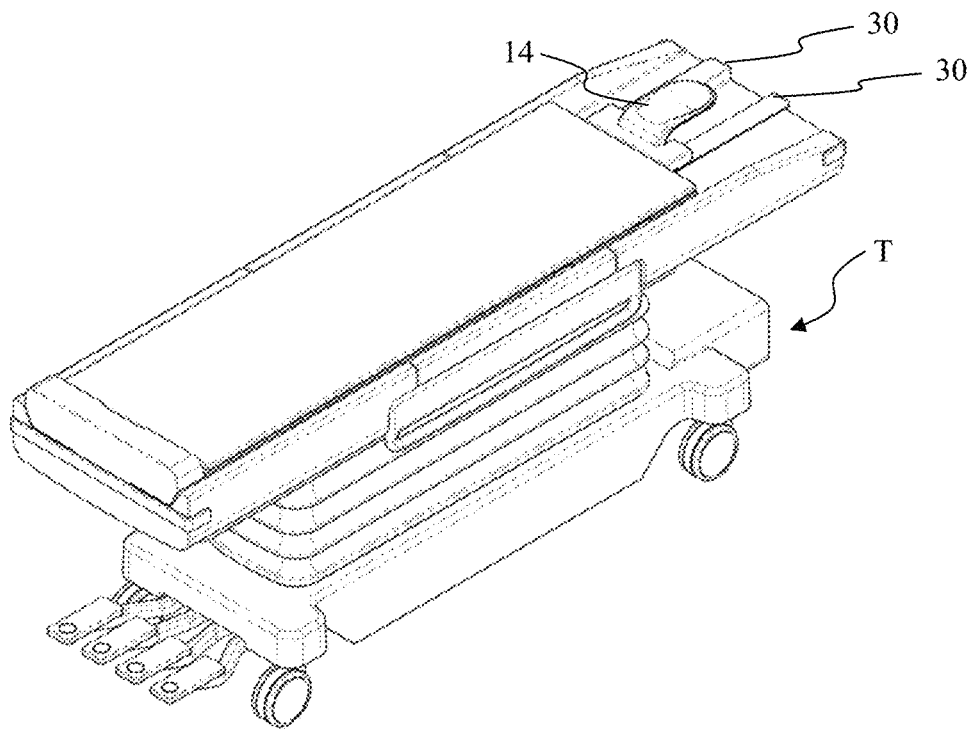
FIG. 10 is a diagram illustrating a perspective view of a transporter, such as an MRI table, for use with a head coil system for enhancing and/or optimizing MRI, as shown in FIGS. 2-9, in accordance with an embodiment of the present disclosure.

Referring to FIG. 10, this diagram illustrates, in a perspective view, a transporter T, such as an MRI table, for use with a head coil system S for enhancing and/or optimizing MRI, as shown in FIGS. 2-9, in accordance with an embodiment of the present disclosure. The head coil system S is optionally adjustable and further comprises at least one of: at least one guide (not shown) configured to engage at least one corresponding rail 30 of the transporter T and to align the tongue portion 14 with the lower portion 11 and the opposing side portions 13; and at least one rail (not shown) configured to engage at least one corresponding guide (not shown) of the transporter T and to align the tongue portion 14 with the lower portion 11 and the opposing side portions 13 (See also FIGS. 11 and 14).

Figure 11:
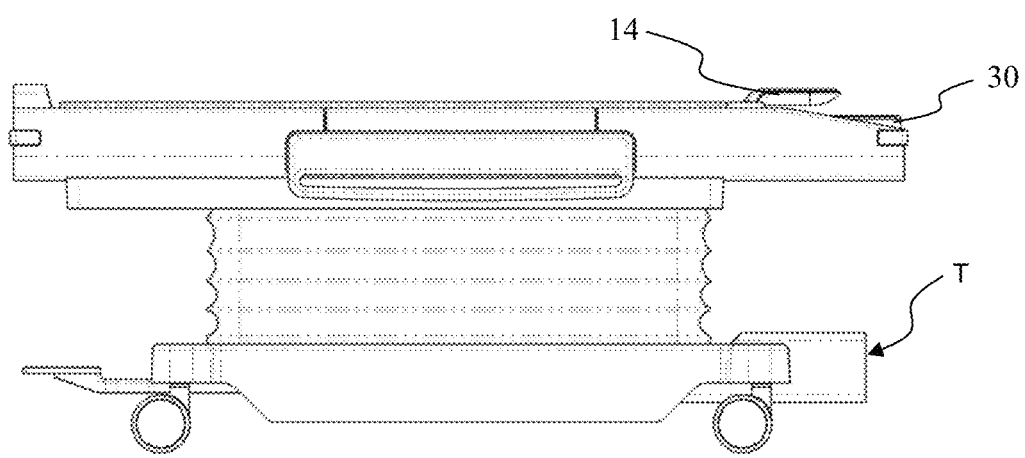
FIG. 11 is a diagram illustrating a side view of a transporter, such as an MRI table, as shown in FIG. 10, for use with a head coil system for enhancing and/or optimizing MRI, as shown in FIGS. 2-9, in accordance with an embodiment of the present disclosure.

Referring to FIG. 11, this diagram illustrates, in a side view, a transporter T, such as an MRI table, as shown in FIG. 10, for use with a head coil system S for enhancing and/or optimizing MRI, as shown in FIGS. 2-9, in accordance with an embodiment of the present disclosure. The head coil system S is optionally adjustable and further comprises at least one of: at least one guide (not shown) configured to engage at least one corresponding rail 30 of the transporter T and to align the tongue portion 14 with the lower portion 11 and the opposing side portions 13; and at least one rail (not shown) configured to engage at least one corresponding guide (not shown) of the transporter T and to align the tongue portion 14 with the lower portion 11 and the opposing side portions 13 (See also FIGS. 10 and 14).

Figure 12:
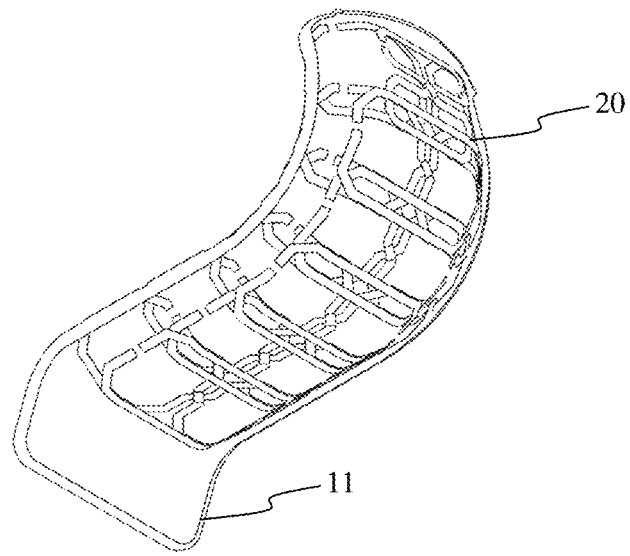
FIG. 12 is a diagram illustrating a perspective view of a lower portion of a head coil system for enhancing and/or optimizing MRI, as shown in FIGS. 2-9, the lower portion optionally comprising RF coils, in accordance with an embodiment of the present disclosure.

Referring to FIG. 12, this diagram illustrates, in a perspective view, a lower portion 11 of a head coil system S for enhancing and/or optimizing MRI, as shown in FIGS. 2-9, the lower portion 11 optionally comprising RF coils 20, in accordance with an embodiment of the present disclosure. The head coil system S is optionally adjustable.

Figure 13:
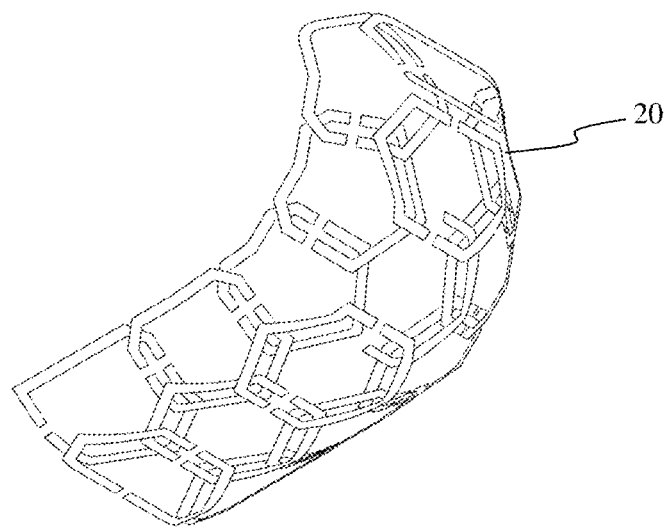
FIG. 13 is a diagram illustrating a perspective view RF coils of a lower portion or a tongue portion, as shown in FIG. 12, in accordance with alternative embodiments of the present disclosure.

Referring to FIG. 13, this diagram illustrates, in a perspective view, RF coils 20 of a lower portion 11, as shown in FIG. 12, in accordance with an embodiment of the present disclosure. Each at least one RF coil 20 comprises at least one configuration of a circular shape and a butterfly shape. The at least one RF coil 20 comprises a plurality of RF coil 20 having an overlapping configuration.

Figure 14A:
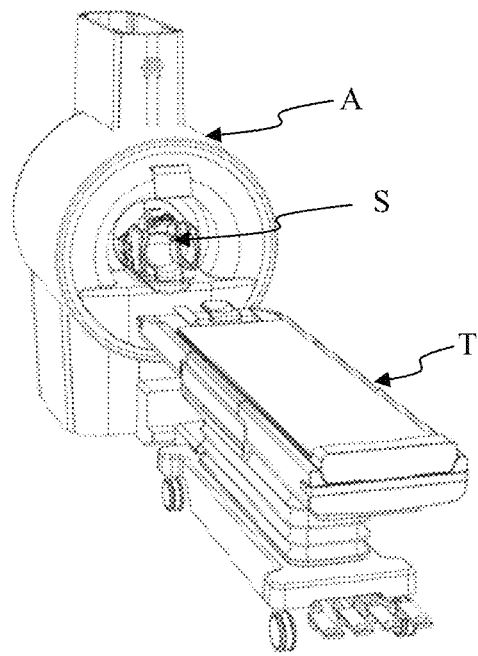
FIG. 14A is a diagram illustrating a perspective view of a head coil system, as shown in FIGS. 2-11, for use with an MRI machine, in accordance with an embodiment of the present disclosure.

Referring to FIG. 14A, this diagram illustrates, in a perspective view, a head coil system S, as shown in FIGS. 2-11, for use with an MRI machine A, the head coil system S, optionally adjustable, comprising upper and lower portions 12, 11, opposing side portions 13, and a tongue portion 14, the tongue portion 14 engageable with the lower portion 11 and the opposing side portions 13, the tongue portion 14 capable of coupling with a transporter T, wherein the upper and lower portions 12, 11 and the opposing side portions 13 are storable in relation to the MRI machine A, and wherein the tongue portion 14 is disengaged from the lower portion 11 and the opposing side portions 13, such as when the system S is not in use, in accordance with an embodiment of the present disclosure.

Still referring to FIG. 14A, by using the head coil system S, optionally adjustable, a patient's head is comfortably disposed on the tongue portion 14, wherein fine adjustments may be made to any sub-portions thereof before the patient's head enters the housing 10. The transporter T is easily moved toward the MRI machine A, wherein the tongue portion 14 readily engages and/or registers with the lower portion 11 and the opposing side portions 13 by way of at least one guide and at least one rail. While registered, if using an adjustable embodiment of the system S, medical personnel, such as an MRI technician may adjust the upper portion 12 in relation to the opposing portions 13 and may adjust the opposing portions 13 in relation to at least one of the lower portion 11 and the tongue portion 14 by way of articulation, disposition, and engagement. Further, fine adjustments may be made by way of articulation, disposition, and engagement of any sub-portions thereof.

Figure 14B:
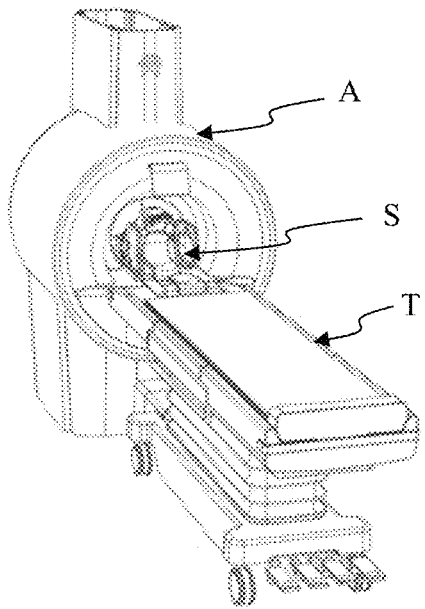
FIG. 14B is a diagram illustrating a perspective view of a head coil system for use with an MRI machine, as shown in FIG. 14A, in accordance with an embodiment of the present disclosure.

Referring to FIG. 14B, this diagram illustrates, in a perspective view, a head coil system S for use with an MRI machine A, as shown in FIG. 14A, the optionally adjustable head coil system S comprising upper and lower portions 12, 11, opposing side portions 13, and a tongue portion 14, the tongue portion 14 engageable with the lower portion 11 and the opposing side portions 13, the tongue portion 14 capable of coupling with the transporter T, wherein the upper and lower portions 12, 11 and the opposing side portions 13 are slidable in relation to the MRI machine A, and wherein the tongue portion 14 is being engaged with the lower portion 11 and the opposing side portions 13, such as by rolling the transporter T toward the MRI machine A, in accordance with an embodiment of the present disclosure.

Figure 14C:
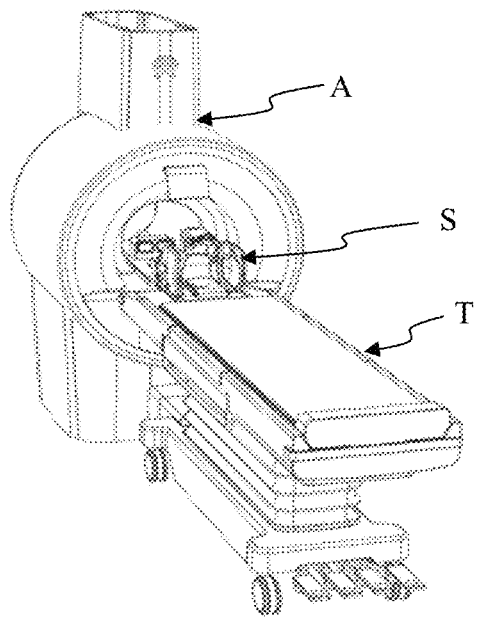
FIG. 14C is a diagram illustrating a perspective view of a head coil system for use with an MRI machine, as shown in FIG. 14A, in accordance with an embodiment of the present disclosure.

Referring to FIG. 14C, this diagram illustrates, in a perspective view, a head coil system S for use with an MRI machine A, as shown in FIG. 14A, the system S comprising upper and lower portions 12, 11, opposing side portions 13, and a tongue portion 14, the tongue portion 14 engageable with the lower portion 11 and the opposing side portions 13, the tongue portion 14 capable of coupling with the transporter T, wherein the upper and lower portions 12, 11 and the opposing side portions 13 are slidable in relation to the MRI machine A, and wherein the tongue portion 14 is engaged with the lower portion 11 and the opposing side portions 13, such as by rolling the transporter T toward the MRI machine A and by sliding the upper and lower portions 12, 11 and the opposing side portions 13 outward from the MRI machine A until the tongue portion 14 is fully engaged with the lower portion 11 and the opposing side portions 13, in accordance with an embodiment of the present disclosure.

Figure 14D:
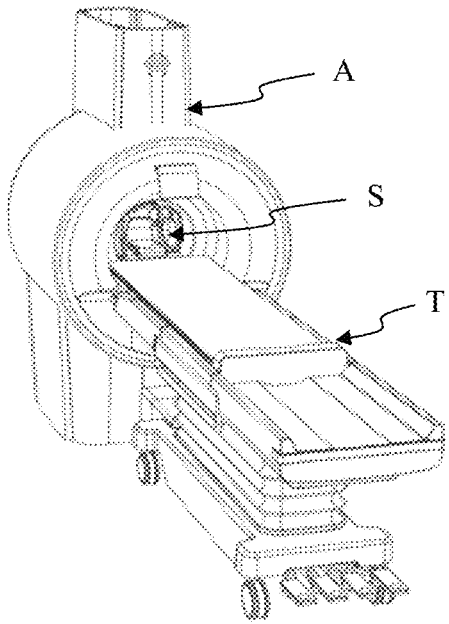
FIG. 14D is a diagram illustrating a perspective view of a head coil system for use with an MRI machine, as shown in FIG. 14A, in accordance with an embodiment of the present disclosure.

Referring to FIG. 14D, this diagram illustrates, in a perspective view, a head coil system S for use with an MRI machine A, as shown in FIG. 14A, the system S comprising upper and lower portions 12, 11, opposing side portions 13, and a tongue portion 14, the tongue portion 14 engageable with the lower portion 11 and opposing side portions 13, the tongue portion 14 capable of coupling with the transporter T, wherein the upper and lower portions 12, 11 and the opposing side portions 13 are slidable in relation to the MRI machine A, such as into (and from) the MRI machine A, and wherein the tongue portion 14 is fully engaged with the lower portion 11 and the opposing side portions 13, such as by rolling the transporter T toward the MRI machine A until the tongue portion 14 is fully engaged with the lower portion 11 and the opposing side portions 13 and continuing to roll the transporter T toward the MRI machine A until the system S is fully disposed within the MRI machine A, whereby the system S is ready for use, in accordance with an embodiment of the present disclosure.

Referring back to FIGS. 14A-14D, the housing of the head coil system S may be adjustable or, alternatively, fixed or integrally formed, wherein the housing is storable in the MRI machine A and deployable therefrom for use. In some embodiments of the present disclosure, the transporter T comprises an MRI table, whereby a need for a stretcher is eliminated. In so eliminating the need for a separate stretcher, otherwise typically required in relation to related art MRI systems, an emergency patient can be more rapidly imaged in order to accelerate diagnosis and therapy. In a transporter T that comprises an MRI table, the related art need to transfer a patient from a related art stretcher to an MRI table is eliminated. The housing of the fixed head coil system is configured storage in an MRI machine A, e.g., by sliding the housing into the MRI machine A when not in use, and for deployment of the housing of the fixed head coil system by sliding the housing from the MRI machine for use, whereby a need for moving a related art head coil from a cabinet is eliminated. In the fixed head coil system, the tongue portion 14 is dockable with the lower portion 11 by moving the transporter T to the MRI machine A, thereby efficiently disposing the fixed head coil system in relation to a head of a patient, and thereby efficiently readying the head of the patient for imaging. In the fixed head coil system, the tongue portion 14 is undockable from the lower portion 11 by moving the transporter T from the MRI machine A, thereby efficiently readying the patient for therapy.

Referring to FIG. 15, this diagram illustrates, in a section view, a head coil system S for enhancing and/or optimizing MRI in a closed position, wherein at least one overlapping portion 15, such as at least one overlapping lip, forms a cavity or volume V, such as a substantially circular scanning surface or scanning bore, in accordance with an embodiment of the present disclosure. The head coil system S is optionally adjustable. At least one of the upper portion 12, the lower portion 11, and the tongue portion 14 is configured to overlap and engage the opposing side portions 13 by way of an overlapping lip structure 15 for eliminating any gaps between each at least one RF coil 20 and ensuring decoupling of each at least one RF coil 20 in the closed position, whereby a scanning volume V, such as a substantially circular scanning, is provided (See also FIG. 15).

Figure 16:
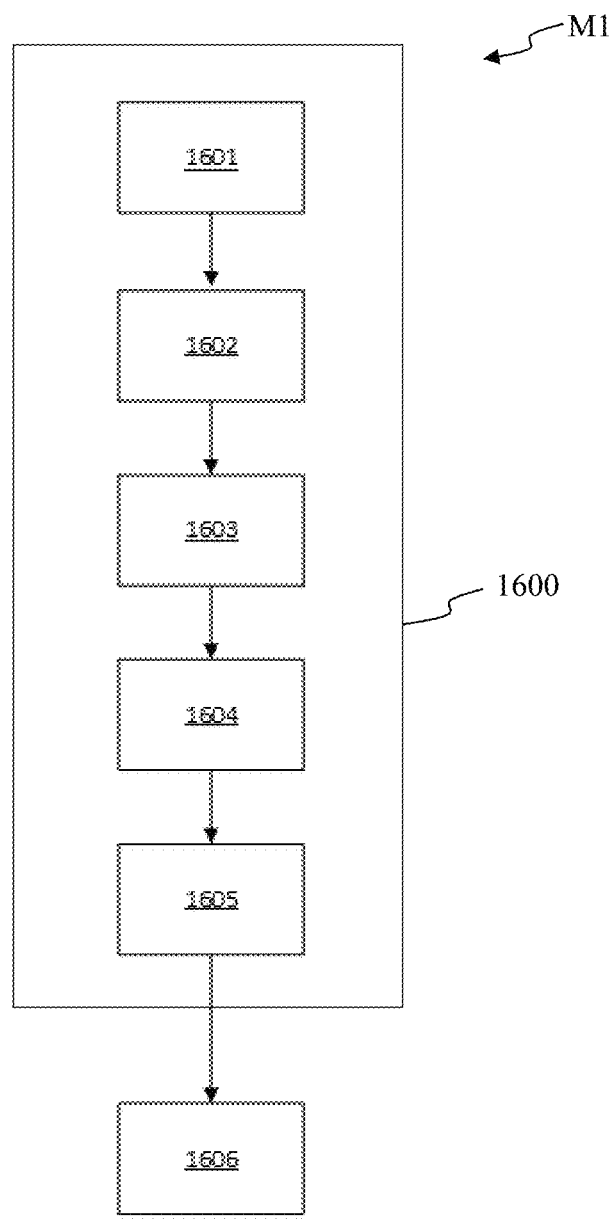
FIG. 16 is a flow diagram illustrating a method of fabricating a head coil system for enhancing and/or optimizing MRI, in accordance with an embodiment of the present disclosure.

Referring to FIG. 16, this flow diagram illustrates a method M1 of fabricating a head coil system S for enhancing and/or optimizing MRI, in accordance with an embodiment of the present disclosure. The head coil system S is optionally adjustable. The method M1 of fabricating a head coil system S for enhancing and/or optimizing magnetic resonance imaging, comprises providing a housing 10 comprising at least one portion, as indicated by block 1600, providing the at least one portion comprising: providing a lower portion 11, an upper portion 12, and opposing side portions 13, as indicated by block 1601; optionally providing each at least one portion in movable relation to any other at least one portion for facilitating adjustability, as indicated by block 1602; configuring each portion to accommodate at least one RF coil 20, as indicated by block 1603; optionally configuring the upper and lower portions each to overlap and engage the opposing side portions 13 for facilitating decoupling the at least one RF coil 20, as indicated by block 1604; optionally configuring the lower portion 11 as engageable with the opposing side portions 13, as indicated by block 1605; and providing a tongue portion 14 optionally in movable relation to any other at least one portion for facilitating at least one of adjustability and dockability, providing the tongue portion 14 comprising configuring the tongue portion 14 to be engageable with the lower portion 11, and configuring the tongue portion 14 to be fixably couple-able with a transporter T, as indicated by block 1606.

Figure 17:
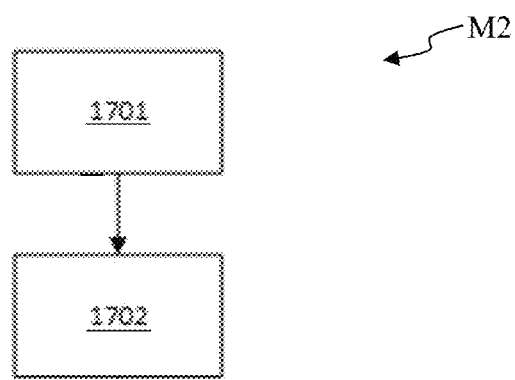
FIG. 17 is a flow diagram illustrating a method of fabricating a head coil system for enhancing and/or optimizing MRI, in accordance with an embodiment of the present disclosure.

Referring to FIG. 17, this flow diagram illustrates a method M2 of fabricating a coil system S for enhancing and/or optimizing magnetic resonance imaging comprises: providing a housing 10, providing the housing 10 comprising providing a plurality of housing portions, providing the plurality of housing portions comprising providing a lower housing portion 11, an upper housing portion 12, and opposing side housing portions 13, providing the plurality of housing portions comprising: configuring each housing portion to accommodate at least one RF coil 20, configuring each of the upper and lower housing portions 12, 11 to overlap and engage the opposing side housing portions 13 for facilitating decoupling the at least one RF coil 20, and configuring the lower housing portion 11 to engage with the opposing side housing portions 13, as indicated by block 1701; and providing a tongue portion 14 in movable relation to each housing portion for facilitating adjustability, providing the tongue portion 14 comprising configuring the tongue portion to: slidably engage with the lower housing portion 11, fixably couple with a transporter T, and overlap each opposing side housing portion 13 in a closed position, as indicated by block 1702, providing the plurality of housing portions further comprising configuring each housing portion to independently move in relation to any other housing portion and in relation to the tongue portion 14 for facilitating adjustability, providing the plurality of housing portions further comprising configuring each housing portion to overlap another housing portion in a closed position, providing the tongue portion 14 comprising providing an overlapping lip structure and configuring the tongue portion 14 to overlap and engage the opposing side housing portions 13 by way of the overlapping lip structure for eliminating any gaps between each at least one RF coil 20 and ensuring decoupling of each at least one RF coil 20 in the closed position, and providing the tongue portion 14 comprising configuring the tongue portion 14 to facilitate adjustability by way of at least one fine adjustment feature comprising at least one of an elastic material and a polymeric material having a memory property, in accordance with an embodiment of the present disclosure.

Figure 18:
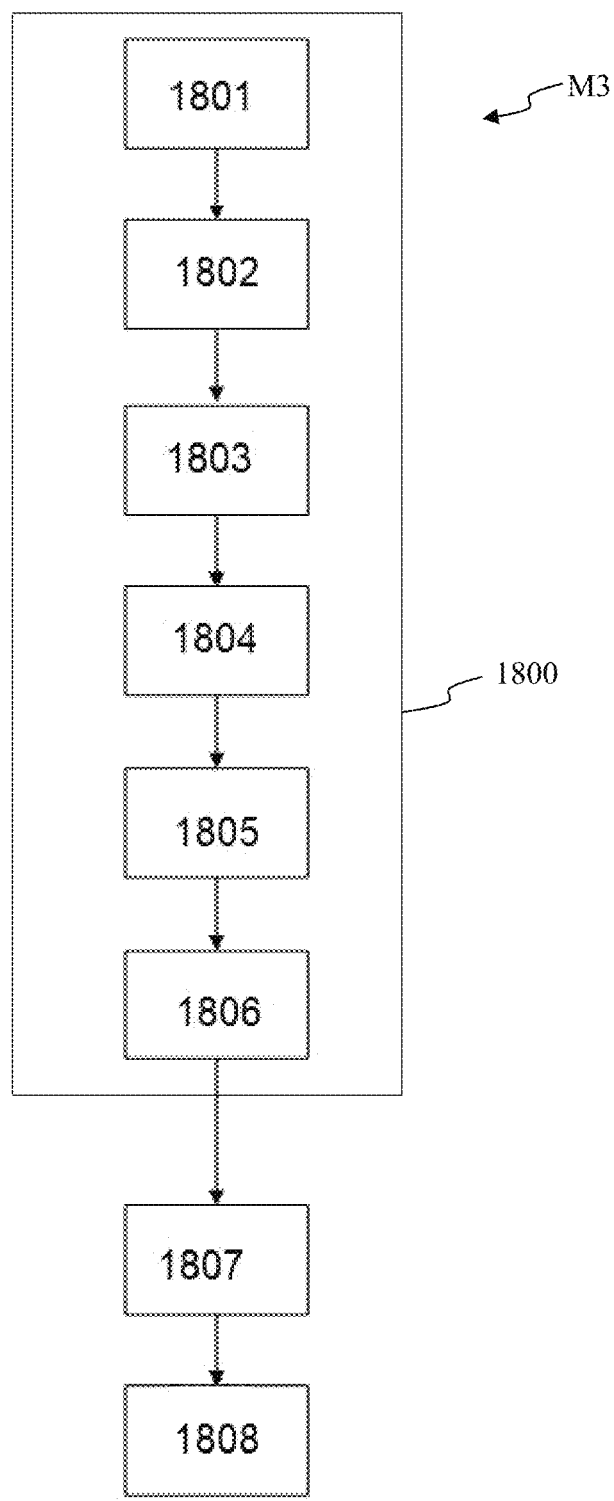
FIG. 18 is a flow diagram illustrating a method of enhancing and/or optimizing MRI by way of a head coil system, in accordance with an embodiment of the present disclosure.

Referring to FIG. 18, this flow diagram illustrates a method M3 of enhancing and/or optimizing MRI by way of a head coil system S, in accordance with an embodiment of the present disclosure. The head coil system S is optionally adjustable. The method M3 of enhancing and/or optimizing magnetic resonance imaging by way of a head coil system S, comprises: providing the head coil system S, as indicated by block 1800, providing the adjustable head coil system S comprising providing a housing 10 comprising at least one portion, as indicated by block 1801, providing the at least one portion comprising: providing a lower portion 11, an upper portion 12, and opposing side portions 13, as indicated by block 1802; optionally providing each at least one portion in movable relation to any other at least one portion for facilitating adjustability, as indicated by block 1803; configuring each portion to accommodate at least one RF coil 20, as indicated by block 1804; optionally configuring the upper and lower portions 12, 11 each to overlap and engage the opposing side portions 13 for facilitating decoupling the at least one RF coil 20, as indicated by block 1805; optionally configuring the lower portion 11 as engageable with the opposing side portions 13, as indicated by block 1806; and providing a tongue portion 14 in movable relation to any other at least one portion for facilitating at least one of adjustability and dockability, providing the tongue portion 14 comprising, configuring the tongue portion 14 to be engageable with the lower portion 11, and configuring the tongue portion 14 to be fixably couple-able with a transporter T, as indicated by block 1807; and coupling the tongue portion 14 with the transporter T, as indicated by block 1808.

Still referring to FIG. 18, the method M3 further comprises: disposing a head of a subject on the tongue portion 14; optionally adjusting the tongue portion 14 to specifically accommodate the head; and moving the tongue portion 14, by way of the transporter T, in relation to the lower portion 11 and the opposing side portions 13, thereby overlapping and engaging the upper portion and the lower portion in relation to the opposing side portions. The method M3 further comprises adjusting at least one portion to specifically further accommodate the head.

Still referring to FIG. 18, in an embodiment wherein the head coil S is fixed, rather than adjustable, the method M3 further comprises: providing the transporter T, wherein the transporter T comprises an MRI table, thereby eliminating a need for a stretcher. The method M3 further comprises: storing the housing of the head coil system S by sliding the housing into an MRI machine A; and deploying the housing of the head coil system S by sliding the housing from the MRI machine A for use, thereby eliminating a need for moving a head coil from a cabinet. The method M3 further comprises: docking the tongue portion 14 with the lower portion 11 by moving the transporter T to the MRI machine A, thereby efficiently disposing the head coil system S in relation to a head of a patient, and thereby efficiently readying the head of the patient for imaging. The method M3 further comprises: undocking the tongue portion 14 from the lower portion 11 by moving the transporter T from the MRI machine A, thereby efficiently readying the patient for therapy.

Figure 19:
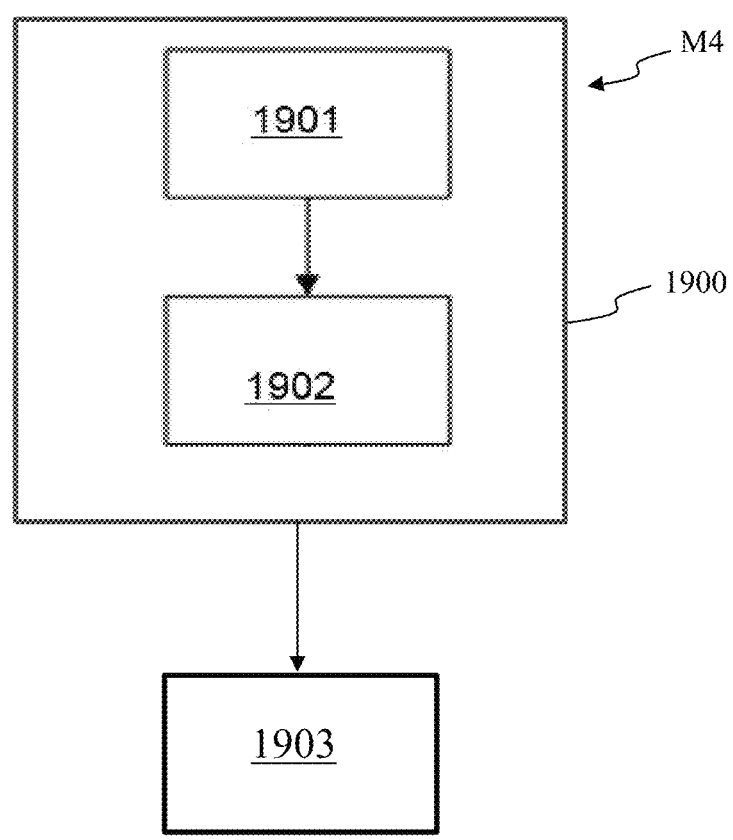
FIG. 19 is a flow diagram illustrating a method of enhancing and/or optimizing MRI by way of a head coil system, in accordance with an embodiment of the present disclosure.

Referring to FIG. 19, this flow diagram illustrates a method M4 of enhancing and/or optimizing magnetic resonance imaging, by way of a coil system S, comprises: providing the coil system S, as indicated by block 1900, providing the coil system S comprising: providing a housing 10, providing the housing 10 comprising providing a plurality of housing portions, providing the plurality of housing portions comprising providing a lower housing portion 11, an upper housing portion 12, and opposing side housing portions 13, providing the plurality of housing portions comprising: configuring each housing portion to accommodate at least one RF coil 20, configuring each of the upper and lower housing portions 12, 11 to overlap and engage the opposing side housing portions 13 for facilitating decoupling the at least one RF coil 20, and configuring the lower housing portion 11 to engage with the opposing side housing portions 13, as indicated by block 1901; and providing a tongue portion 14 in movable relation to each housing portion for facilitating adjustability, providing the tongue portion 14 comprising configuring the tongue portion to: slidably engage with the lower housing portion 11, fixably couple with a transporter T, and overlap each opposing side housing portion 13 in a closed position, as indicated by block 1902, providing the plurality of housing portions further comprising configuring each housing portion to independently move in relation to any other housing portion and in relation to the tongue portion 14 for facilitating adjustability, providing the plurality of housing portions further comprising configuring each housing portion to overlap another housing portion in a closed position, providing the tongue portion 14 comprising providing an overlapping lip structure and configuring the tongue portion 14 to overlap and engage the opposing side housing portions 13 by way of the overlapping lip structure for eliminating any gaps between each at least one RF coil 20 and ensuring decoupling of each at least one RF coil 20 in the closed position, and providing the tongue portion 14 comprising configuring the tongue portion 14 to facilitate adjustability by way of at least one fine adjustment feature comprising at least one of an elastic material and a polymeric material having a memory property; and operating the coil system, as indicated by block 1903, in accordance with an embodiment of the present disclosure.

Information, as herein shown and described in detail, is fully capable of attaining the above-described solutions, objects, benefits, and/or advantages of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments, as regarded by those of ordinary skill in the art, are hereby expressly incorporated by reference and are intended to be encompassed by the present claims.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, various changes and modifications in form, material, work-piece, and fabrication material detail may be made, as well as any combination or permutation of any feature(s), as herein described or shown in the accompanying drawing(s), without departing from the spirit and scope of the present disclosure, as set forth in the appended claims, as may be apparent to those of ordinary skill in the art, are also encompassed by the present disclosure.

INDUSTRIAL APPLICABILITY

The present disclosure industrially applies to magnetic resonance imaging (MRI) systems and methods. More particularly, the present disclosure industrially applies to RF coil systems and methods for MRI. Even more particularly, the present disclosure industrially applies to RF head coil systems and methods for MRI.

What is claimed:

1. A coil system for enhancing and/or optimizing magnetic resonance imaging, the system comprising:
 a housing comprising a plurality of housing portions, the plurality of housing portions comprising a lower housing portion, an upper housing portion, and opposing side housing portions, each housing portion configured to accommodate at least one radio-frequency coil, the upper and lower housing portions each configured to overlap and engage the opposing side housing portions for facilitating decoupling the at least one radio-frequency coil, and the lower housing portion configured to engage with the opposing side housing portions; and
 a tongue portion in movable relation to each housing portion for facilitating adjustability, the tongue portion configured to: slidably engage with the lower housing portion, fixably couple with a transporter, and overlap each opposing side housing portion in a closed position,
 each housing portion further configured to independently move in relation to any other housing portion and in relation to the tongue portion for facilitating adjustability,
 each housing portion configured to overlap another housing portion in a closed position,
 the tongue portion comprising an overlapping lip structure and configured to overlap and engage the opposing side housing portions by way of the overlapping lip structure for eliminating any gaps between each at least one radio-frequency coil and ensuring decoupling of each at least one radio-frequency coil in the closed position, and
 the tongue portion configured to facilitate adjustability by way of at least one fine adjustment feature comprising at least one of an elastic material and a polymeric material having a memory property.

2. The system of claim 1, wherein the housing is configured to accommodate a head of any given subject by way of adjustability of each housing portion in relation to another housing portion.

3. The system of claim 1,
wherein each housing portion is spaced apart from another housing portion in an open position,
wherein the tongue portion is spaced apart from each housing portion in an open position,
wherein the tongue portion is movable for further facilitating dockability,
wherein at least one of each housing portion and the tongue portion is further configured to facilitate fine adjustability, and
wherein each housing portion comprises a plurality of housing sub-portions, each housing sub-portion configured to articulate in relation to another housing sub-portion.

4. The system of claim 3, wherein each housing sub-portion is configured to articulate in relation to another housing sub-portion by way of at least one of a hinge, a pin, a ball joint, and a slider.

5. The system of claim 1, further comprising at least one of:
at least one guide configured to engage at least one corresponding rail of the transporter and to align the tongue portion with the lower housing portion and the opposing side housing portions; and
at least one rail configured to engage at least one corresponding guide of the transporter and to align the tongue portion with the lower housing portion and the opposing side housing portions.

6. The system of claim 1, wherein each housing portion is further configured to overlap at least one radio-frequency coil with another at least one radio-frequency coil.

7. The system of claim 1, wherein each housing portion is further configured to accommodate the at least one radio-frequency coil comprising at least one shape of: a circular shape and a butterfly shape.

8. A method of fabricating a coil system for enhancing and/or optimizing magnetic resonance imaging, the method comprising:
providing a housing, providing the housing comprising providing a plurality of housing portions, providing the plurality of housing portions comprising providing a lower housing portion, an upper housing portion, and opposing side housing portions, providing the plurality of housing portions comprising: configuring each housing portion to accommodate at least one radio-frequency coil, configuring each of the upper and lower housing portions to overlap and engage the opposing side housing portions for facilitating decoupling the at least one radio-frequency coil, and configuring the lower housing portion to engage with the opposing side housing portions; and
providing a tongue portion in movable relation to each housing portion for facilitating adjustability, providing the tongue portion comprising configuring the tongue portion to: slidably engage with the lower housing portion, fixably couple with a transporter, and overlap each opposing side housing portion in a closed position,
providing the plurality of housing portions further comprising configuring each housing portion to independently move in relation to any other housing portion and in relation to the tongue portion for facilitating adjustability,
providing the plurality of housing portions further comprising configuring each housing portion to overlap another housing portion in a closed position,
providing the tongue portion comprising providing an overlapping lip structure and configuring the tongue portion to overlap and engage the opposing side housing portions by way of the overlapping lip structure for eliminating any gaps between each at least one radio-frequency coil and ensuring decoupling of each at least one radio-frequency coil in the closed position, and
providing the tongue portion comprising configuring the tongue portion to facilitate adjustability by way of at least one fine adjustment feature comprising at least one of an elastic material and a polymeric material having a memory property.

9. The method of claim 8, wherein providing the housing comprises configuring the housing to accommodate a head of any given subject by way of adjustability of each housing portion in relation to another housing portion.

10. The method of claim 8,
wherein providing the plurality of housing portions comprises configuring each housing portion to space apart from another housing portion in an open position,
wherein providing the tongue portion comprises configuring the tongue portion to space apart from each housing portion in an open position,
wherein providing the tongue portion comprises configuring the tongue portion to move for further facilitating dockability,
wherein providing the plurality of housing portions further comprises configuring each housing portion to facilitate fine adjustability,
wherein providing the tongue portion comprises further configuring the tongue portion to facilitate fine adjustability, and
wherein providing the plurality of housing portions further comprises providing a plurality of housing sub-portions, providing the plurality of housing sub-portions comprising configuring each housing sub-portion articulate in relation to another housing sub-portion.

11. The method of claim 10, wherein configuring each housing sub-portion further comprises configuring each housing sub-portion to articulate in relation to another housing sub-portion by way of at least one of a hinge, a pin, a ball joint, and a slider.

12. The method of claim 8, further comprising at least one of:
providing at least one guide configured to engage at least one corresponding rail of the transporter and to align the tongue portion with the lower housing portion and the opposing side housing portions; and
providing at least one rail configured to engage at least one corresponding guide of the transporter and to align the tongue portion with the lower housing portion and the opposing side housing portions.

13. The method of claim 12, wherein configuring each housing portion further comprises configuring each housing portion to overlap at least one radio-frequency coil with another at least one radio-frequency coil.

14. The method of claim 12, wherein configuring each housing portion further comprises configuring each housing portion to accommodate the at least one radio-frequency coil comprising at least one shape of: a circular shape and a butterfly shape.

15. A method of enhancing and/or optimizing magnetic resonance imaging by way of a coil system, the method comprising:

providing the coil system, providing the coil system comprising:
- providing a housing, providing the housing comprising providing a plurality of housing portions, providing the plurality of housing portions comprising providing a lower housing portion, an upper housing portion, and opposing side housing portions, providing the plurality of housing portions comprising: configuring each housing portion to accommodate at least one radio-frequency coil, configuring each of the upper and lower housing portions to overlap and engage the opposing side housing portions for facilitating decoupling the at least one radio-frequency coil, and configuring the lower housing portion to engage with the opposing side housing portions; and
- providing a tongue portion in movable relation to each housing portion for facilitating adjustability, providing the tongue portion comprising configuring the tongue portion to: slidably engage with the lower housing portion, fixably couple with a transporter, and overlap each opposing side housing portion in a closed position,
- providing the plurality of housing portions further comprising configuring each housing portion to independently move in relation to any other housing portion and in relation to the tongue portion for facilitating adjustability,
- providing the plurality of housing portions further comprising configuring each housing portion to overlap another housing portion in a closed position,
- providing the tongue portion comprising providing an overlapping lip structure and configuring the tongue portion to overlap and engage the opposing side housing portions by way of the overlapping lip structure for eliminating any gaps between each at least one radio-frequency coil and ensuring decoupling of each at least one radio-frequency coil in the closed position, and
- providing the tongue portion comprising configuring the tongue portion to facilitate adjustability by way of at least one fine adjustment feature comprising at least one of an elastic material and a polymeric material having a memory property; and operating the coil system.

16. The method of claim 15, wherein providing the housing comprises configuring the housing to accommodate a head of any given subject by way of adjustability of each housing portion in relation to another housing portion.

17. The method of claim 15,
- wherein providing the plurality of housing portions comprises configuring each housing portion to space apart from another housing portion in an open position,
- wherein providing the tongue portion comprises configuring the tongue portion to space apart from each housing portion in an open position,
- wherein providing the tongue portion comprises configuring the tongue portion to move for further facilitating dockability,
- wherein providing the plurality of housing portions further comprises configuring each housing portion to facilitate fine adjustability,
- wherein providing the tongue portion comprises further configuring the tongue portion to facilitate fine adjustability, and
- wherein providing the plurality of housing portions further comprises providing a plurality of housing sub-portions, providing the plurality of housing sub-portions comprising configuring each housing sub-portion articulate in relation to another housing sub-portion.

18. The method of claim 17, wherein configuring each housing sub-portion further comprises configuring each housing sub-portion to articulate in relation to another housing sub-portion by way of at least one of a hinge, a pin, a ball joint, and a slider.

19. The method of claim 15, further comprising at least one of:
- providing at least one guide configured to engage at least one corresponding rail of the transporter and to align the tongue portion with the lower housing portion and the opposing side housing portions; and
- providing at least one rail configured to engage at least one corresponding guide of the transporter and to align the tongue portion with the lower housing portion and the opposing side housing portions.

20. The method of claim 19, wherein at least one of:
- configuring each housing portion further comprises configuring each housing portion to overlap at least one radio-frequency coil with another at least one radio-frequency coil, and
- configuring each housing portion further comprises configuring each housing portion to accommodate the at least one radio-frequency coil comprising at least one shape of: a circular shape and a butterfly shape.

* * * * *